US010758189B2

United States Patent
Smits et al.

(10) Patent No.: US 10,758,189 B2
(45) Date of Patent: Sep. 1, 2020

(54) METHOD AND APPARATUS FOR USE IN MONITORING AND IDENTIFYING ABNORMAL VALUES OF A PHYSIOLOGICAL CHARACTERISTIC OF A SUBJECT

(71) Applicant: KONINKLIJKE PHILIPS N.V., Eindhoven (NL)

(72) Inventors: Tine Smits, Vosselaar (BE); Jennifer Caffarel, Eindhoven (NL); Emile Josephus Carlos Kelkboom, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 542 days.

(21) Appl. No.: 14/647,832

(22) PCT Filed: Dec. 11, 2013

(86) PCT No.: PCT/IB2013/060811
§ 371 (c)(1),
(2) Date: May 28, 2015

(87) PCT Pub. No.: WO2014/091426
PCT Pub. Date: Jun. 19, 2014

(65) Prior Publication Data
US 2015/0342539 A1    Dec. 3, 2015

(30) Foreign Application Priority Data

Dec. 13, 2012  (EP) .................................... 12196989

(51) Int. Cl.
*A61B 5/053* (2006.01)
*A61B 5/00* (2006.01)
*A61B 5/08* (2006.01)

(52) U.S. Cl.
CPC .............. *A61B 5/7282* (2013.01); *A61B 5/00* (2013.01); *A61B 5/053* (2013.01); *A61B 5/0537* (2013.01);
(Continued)

(58) Field of Classification Search
CPC ..... A61B 5/746; A61B 5/7271; A61B 5/7275; A61B 5/7282; A61B 5/7278; A61B 5/7246
See application file for complete search history.

(56) References Cited

U.S. PATENT DOCUMENTS 6,473,640 B1   10/2002  Erlebacher
6,996,434 B2   2/2006   Marcovecchio et al.
(Continued)

FOREIGN PATENT DOCUMENTS

WO   2004050178 A1   6/2004
WO   2007105996 A1   9/2007

OTHER PUBLICATIONS

Webster, John G., and John W. Clark. Medical Instrumentation: Application and Design. Wiley, 2010 (Year: 2010).*
(Continued)

*Primary Examiner* — Niketa I Patel
*Assistant Examiner* — Nathan A Baldwin (57) ABSTRACT

There is provided a method for use in monitoring a physiological characteristic of a subject, the method comprising receiving a value of the physiological characteristic of the subject; determining whether the received physiological characteristic value is normal using a range of normal variability of the physiological characteristic for the subject calculated using a set of previous values of the physiological characteristic for the subject; and in the event that the received physiological characteristic value is determined to
(Continued)

be normal, updating the range of normal variability using the received physiological characteristic value.

9 Claims, 5 Drawing Sheets

(52) U.S. Cl.
CPC .............. *A61B 5/08* (2013.01); *A61B 5/0809* (2013.01); *A61B 5/4878* (2013.01); *A61B 5/7246* (2013.01)

(56) References Cited

U.S. PATENT DOCUMENTS

| | | | | |
|---|---|---|---|---|
| 2004/0059238 | A1* | 3/2004 | Fischell | ............... A61B 5/0031 |
| | | | | 600/515 |
| 2006/0116596 | A1* | 6/2006 | Zhou | ................... A61B 5/0422 |
| | | | | 600/516 |
| 2007/0142866 | A1 | 6/2007 | Li et al. | |
| 2008/0146891 | A1* | 6/2008 | Wang | .................. G06F 19/3418 |
| | | | | 600/300 |
| 2008/0146981 | A1 | 6/2008 | Greenwald et al. | |

OTHER PUBLICATIONS

Fein et al, "Evaluation of Transthoracic Electrical Impedance in the Diagnosis of Pulmonary Edema", Circulation, vol. 60, 1979, pp. 1156-1160.

Yu et al, "Intrathoracic Impedance Monitoring in Patients With Heart Failure: Correlation With Fluid Status and Feasibility of Early Warning Preceding Hospitalization", Circulation, vol. 112, 2005, pp. 841-848.

* cited by examiner

METHOD AND APPARATUS FOR USE IN MONITORING AND IDENTIFYING ABNORMAL VALUES OF A PHYSIOLOGICAL CHARACTERISTIC OF A SUBJECT

CROSS-REFERENCE TO PRIOR APPLICATIONS

This application is the U.S. National Phase application under 35 U.S.C. § 371 of International Application No. PCT/IB2013/060811, filed on Dec. 11, 2013, which claims the benefit of European Patent Application No. 12196989.3, filed on Dec. 13, 2012. These applications are hereby incorporated by reference herein.

TECHNICAL FIELD OF THE INVENTION

The invention relates to a method and apparatus for use in monitoring and identifying abnormal values of a physiological characteristic of a subject.

BACKGROUND TO THE INVENTION

Pulmonary congestion is a clinical condition that is caused by a number of different diseases such as heart failure or kidney disease. It consists of an accumulation of fluid in the interstitial and alveolar space of the lung following increased blood pressure in the pulmonary capillary vessels that leads to leakage of water from the blood to the lung space. It causes fluid retention and fluid redistribution in the body and leads to symptoms like dyspnea, fatigue, and activity intolerance. Pulmonary congestion resulting from elevated left atrial and left ventricular filling pressures is a main reason for heart failure hospitalization. This condition has a progressive nature and clinical signs and symptoms of pulmonary oedema occur late, typically when the lung fluid has increased at least six-fold from the initial stage of interstitial oedema. This means that pulmonary oedema is often not detected early, and necessary treatment for the patient is delayed.

Bio-impedance measurements, obtained by a bio-impedance monitor (BIM) using, for example, external electrodes or an implanted device to measure the resistance of biological tissue to a small alternating current flowing across a region of interest, e.g. the thorax, can be used to detect pulmonary congestion. The principle underlying this technique is the fact that the electrical impedance (resistance and reactance) of biological tissue is directly linked to the hydration and water content of the tissue, namely intracellular and extra-cellular water. When thoracic fluid accumulates (e.g. during pulmonary congestion), there will be a better conductance of the current resulting in a decreased impedance. By measuring the impedance at different frequencies the resistance of the extracellular water ($R_e$) can be estimated according to the Cole-Cole model. Therefore, measurements of the electrical properties of the tissue can indicate the amount of fluid present in that part of the body.

If external electrodes are used, impedance measurements are influenced by several factors including sensor placement, skin moisture, body dimensions and body posture. It has been found that body dimensions and fat mass are particularly relevant to thoracic impedance measurements, making such measurements subject-specific. Implantable devices are not affected by variations in electrode placement or skin moisture; however, it is known that the measurements made by such devices have variability due to less controlled measurement conditions (the patient may be unaware that a measurement is being taken and so measurements may be obtained in a variety of situations which would cause differing fluid distribution in the body, such as lying down, sitting, walking, or exercising). These factors, combined with the normal variability of bio-impedance measurements, make it challenging to determine when an impedance measurement for a specific patient is abnormal and thus indicative of excess fluid accumulation.

"Intrathoracic Impedance Monitoring in Patients with Heart Failure" by Yu et. al., *Circulation* 112 (2005), 841-848 describes an algorithm that can be used to detect abnormal measurements. The algorithm estimates the baseline impedance (BL) and the short term impedance (STA) on the basis of daily bio-impedance measurements. The baseline acts as a reference that is not sensitive to large deviations of the new measurements. On the other hand, the STA is a filtered estimate of the recent measurements and is more sensitive to large deviations of the measurement. The algorithm raises a flag if the cumulative sum of the difference BL-STA exceeds a certain threshold for consecutive measurements, where BL-STA>X. The disadvantage of the described algorithm is that it does not consider the subject-specific variability of the impedance measurements, e.g. X is constant for each patient. As noted above, it is known that the measurement variability is patient specific, which implies that this method is not optimal and prone to false alarms.

A reliable means of fluid content monitoring would be a valuable tool to improve outcomes in heart failure hospitalizations and reduce healthcare costs. There is therefore a need for an improved method and apparatus that can provide a reliable determination of whether a bio-impedance measurement obtained for a given subject is abnormal for that subject, and thus indicative of ill-health (for example indicative of excessive fluid accumulation in a part of the body where the resistance is relatively low, or, on the other hand, indicative of dehydration of the subject where the resistance is relatively high). Such a method and apparatus could be used in a home or hospital-based monitoring system to detect the presence and progression of pulmonary congestion, as well as for monitoring improvements in the patient's condition as a result of receiving treatment. Such a method and apparatus could also be used in monitoring other physiological characteristics of a subject, such as weight, heart rate, blood pressure, temperature, etc., where low or alternatively high values of the physiological characteristic indicates that the subject has (or the degree to which the subject has) a physiological condition.

SUMMARY OF THE INVENTION

According to a first aspect of the invention, there is provided a method for use in monitoring a physiological characteristic of a subject, the method comprising receiving a value of the physiological characteristic of the subject; determining whether the received physiological characteristic value is normal using a range of normal variability of the physiological characteristic for the subject calculated using a set of previous values of the physiological characteristic for the subject; and in the event that the received physiological characteristic value is determined to be normal, updating the range of normal variability using the received physiological characteristic value.

Preferably, the step of updating the range of normal variability comprises adding the received physiological characteristic value to the set of previous physiological characteristic values, and recalculating the range of normal variability using the set of previous physiological characteristic values.

Preferably, the method further comprises the step of providing an indication that the received physiological characteristic value is abnormal in the event that the received physiological characteristic is not determined to be normal.

In particular embodiments of the invention, the physiological characteristic is the resistance of a part of the body of the subject, and the method further comprises the step of determining an indication of the fluid content in the part of the subject's body using the received resistance value in the event that it is determined that the received resistance value is abnormal.

In preferred embodiments, the step of determining whether the received physiological characteristic value is normal comprises comparing the physiological characteristic value to upper and lower bounds that define the range of normal variability.

In a first specific embodiment, the method is for use in monitoring for low values of the physiological characteristic of the subject, with a low value of the physiological characteristic indicating that the subject has, or the degree to which the subject has, a physiological condition wherein the step of determining whether the received physiological characteristic value is normal further comprises if the received physiological characteristic value is below the lower bound, comparing the number of consecutive received physiological characteristic values that are below the lower bound to a first threshold value, N; and determining that the received physiological characteristic value is abnormal when the number of consecutive received physiological characteristic values below the lower bound of the range of normal variability is equal to or greater than the first threshold value; determining the received physiological characteristic value to be normal if the number of consecutive received physiological characteristic values below the lower bound is less than the first threshold value.

In the first specific embodiment, the method can further comprise the step of, following a determination that the received physiological characteristic value is abnormal, determining whether the number of consecutive received physiological characteristic values that are below the lower bound is equal to the first threshold value, N, and if so, removing one or more physiological characteristic values most recently added to the set of previous physiological characteristic values.

In the first specific embodiment, the step of determining whether the received physiological characteristic value is normal can comprise determining that the received physiological characteristic value is normal if the received physiological characteristic value is above the upper bound.

In the first specific embodiment, the method can further comprise the steps of, following a determination that the received physiological characteristic value is above the upper bound, comparing the number of consecutive received physiological characteristic values that are above the upper bound of the range of normal variability to a second threshold value, M; and if the number of consecutive received resistance values that are above the upper bound exceeds the second threshold value, removing one or more of the lowest physiological characteristic values from the set of previous physiological characteristic values.

In the first specific embodiment, the step of determining whether the received physiological characteristic value is normal can comprise, if the received physiological characteristic value is between the upper bound and lower bound, determining if (i) the number of consecutive physiological characteristic values between the upper bound and the lower bound that have been received is less than or equal to a third threshold value, Z, and (ii) the number of consecutive physiological characteristic values falling below the lower bound received immediately prior to the received consecutive physiological characteristic values between the upper bound and the lower bound is greater than the first threshold value, N; determining that the received physiological characteristic value is normal if one or both of (i) and (ii) are negative; and determining that the received physiological characteristic value is abnormal if both of (i) and (ii) are positive.

In the first specific embodiment, the physiological characteristic can be the resistance of a part of the body of the subject, and the physiological condition is excess fluid content in the part of the body of the subject.

In a second specific embodiment, the method is for use in monitoring for high values of the physiological characteristic of the subject, with a high value of the physiological characteristic indicating that the subject has, or the degree to which the subject has, a physiological condition wherein the step of determining whether the received physiological characteristic value is normal further comprises if the received physiological characteristic value is above the upper bound, comparing the number of consecutive received physiological characteristic values that are above the upper bound to a first threshold value, N; and determining that the received physiological characteristic value is abnormal when the number of consecutive received physiological characteristic values above the upper bound of the range of normal variability is equal to or greater than the first threshold value; determining the received physiological characteristic value to be normal if the number of consecutive received physiological characteristics values above the upper bound is less than the first threshold.

In the second specific embodiment, the method can further comprise the step of, following a determination that the received physiological characteristic value is abnormal, determining whether the number of consecutive received physiological characteristic values that are above the upper bound is equal to the first threshold value, N, and if so, removing one or more physiological characteristic values most recently added to the set of previous physiological characteristic values.

In the second specific embodiment, the step of determining whether the received physiological characteristic value is normal can comprise determining that the received physiological characteristic value is normal if the received physiological characteristic value is below the lower bound.

In the second specific embodiment, the method can further comprise the steps of, following a determination that the received physiological characteristic value is below the lower bound, comparing the number of consecutive received physiological characteristic values that are below the lower bound of the range of normal variability to a second threshold value, M; and if the number of consecutive received resistance values that are below the lower bound exceeds the second threshold value, removing one or more of the highest physiological characteristic values from the set of previous physiological characteristic values.

In the second specific embodiment, the step of determining whether the received physiological characteristic value is normal can comprise, if the received physiological characteristic value is between the upper bound and lower bound, determining if (i) the number of consecutive physiological characteristic values between the upper bound and the lower bound that have been received is less than or equal to a third threshold value, Z, and (ii) the number of consecutive physiological characteristic values being above the upper bound received immediately prior to the received consecutive physiological characteristic values between the upper bound and the lower bound is greater than the first threshold value, N; determining that the received physiological characteristic value is normal if one or both of (i) and (ii) are negative; and determining that the received physiological characteristic value is abnormal if both of (i) and (ii) are positive.

In a second specific embodiment, the physiological characteristic can be the resistance of a part of the body of the subject, and the physiological condition is dehydration of the subject.

In some embodiments, the upper bound and lower bound are determined from an average of the set of previous physiological characteristic values and a measure of the variation of the set of previous physiological characteristic values.

In some embodiments, the measure of the variation is calculated from the standard deviation of the set of previous physiological characteristic values, and maximum and minimum coefficients of variance calculated on the basis of a training set of physiological characteristic values obtained from a plurality of other subjects who do not have abnormal values for the physiological characteristic when the training set of physiological characteristic values is obtained, wherein the measure of the variation comprises (i) the standard deviation of the set of previous physiological characteristic values if the standard deviation is below the maximum coefficient of variance times the average of the set of previous physiological characteristic values and above the minimum coefficient of variance times the average of the set of previous physiological characteristic values; (ii) the product of the average of the set of previous physiological characteristic values and the minimum coefficient of variance if the standard deviation is below the minimum coefficient of variance times the average of the set of previous physiological characteristic values; and (iii) the product of the average of the set of previous physiological characteristic values and the maximum coefficient of variance if the standard deviation is above the maximum coefficient of variance times the average of the set of previous physiological characteristic values.

In some embodiments, the upper bound is given by the sum of the average of the set of previous physiological characteristic values and the measure of the variation, and the lower bound is given by the subtraction of the difference between the average of the set of previous physiological characteristic values and the measure of the variation from the average of the set of previous physiological characteristic values.

In preferred embodiments, the received physiological characteristic value is a resistance value estimated from a measurement of the bio-impedance of the part of the subject's body.

In further preferred embodiments, the received resistance value is the resistance of the extracellular fluid in the part of the subject's body.

According to a second aspect of the invention, there is provided a computer program product, comprising computer readable code embodied therein, the computer readable code being configured such that, on execution by a suitable computer or processor, the computer or processor performs the method described in any preceding claim.

According to a third aspect of the invention, there is provided an apparatus for use in monitoring a physiological characteristic of a subject, the apparatus comprising a processing unit arranged to receive a value of the physiological characteristic of the subject; determine whether the received physiological characteristic value is normal using a range of normal variability of the physiological characteristic for the subject calculated using a set of previous values of the physiological characteristic for the subject; and in the event that the received value of the physiological characteristic is determined to be normal, update the range of normal variability using the received physiological characteristic value.

Various other embodiments of the apparatus are also contemplated in which the processing unit is further configured to execute any of the above-described method steps.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
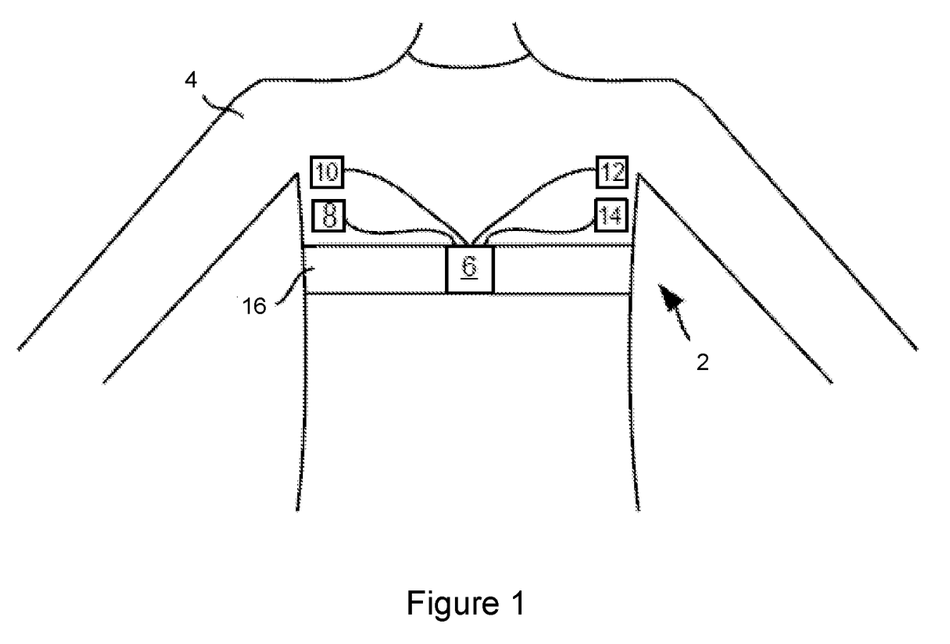
FIG. 1 is an illustration of an apparatus for measuring the fluid content of part of the body of a subject according to an embodiment.

FIG. 1 shows an apparatus for use in monitoring a physiological characteristic of a subject according to the invention. In this particular embodiment, the physiological characteristic is the fluid content of a part of the body of a subject, measured in terms of the resistance of the part of the body of the subject, and thus FIG. 1 shows an apparatus for use in monitoring fluid content in a part of the body of a subject (patient) using bio-impedance measurements that can implement the method according to the invention. However, those skilled in the art will appreciate that the apparatus can be readily adapted for use in monitoring other physiological parameters through the inclusion or use of a suitable sensor. For example, the apparatus can be used to monitor any of a variety of other physiological characteristics, such as weight, blood pressure, temperature, heart rate, etc. using sensors suitable for measuring those characteristics.

The apparatus 2 is shown in FIG. 1 as being worn by or attached to a subject 4 by a strap or belt 16, although it will be appreciated that other arrangements are possible, such as a vest incorporating the apparatus. The apparatus 2 comprises a control unit 6 that is connected to electrodes 8, 10, 12, 14 that are to be attached to, or otherwise placed into contact with, the skin of the subject 4. In the illustrated embodiment, two pairs of electrodes are provided. A first pair of electrodes 8, 12 deliver a small electric current at one or more selected frequencies into the chest of the subject 4. A second pair of electrodes 10, 14, each placed near a respective one of the electrodes 8, 12 in the first pair, are placed on the skin of the subject 4 to measure the differential potential across the chest of the subject 4. Where, as in the illustrated embodiment, the apparatus 2 is to monitor the fluid accumulation in the lungs of the subject 4, the electrodes in each pair are placed on opposite sides of the thorax of the subject 4. The illustrated apparatus 2 is therefore a non-invasive trans-thoracic bio-impedance measurement system.

If the tissue in the body part being measured contains a high level of fluid, it conducts electricity better and thus its impedance is lower than if it contains less fluid. By measuring the impedance at different frequencies the resistance of extracellular fluid ($R_e$) in the tissue can be estimated separately from the resistance of the intracellular fluid ($R_i$) using the Cole-Cole model. In particular, at low measurement frequencies (e.g. approaching 0 Hz) the measured biological tissue impedance is mainly determined by the extracellular fluid content and its characteristics. At these low frequencies, the injected current does not easily pass through cell membranes. At higher frequencies the electrical properties of the biological tissue are determined by both the intracellular and extracellular fluid content as the injected current is able to pass through the cell membranes. Therefore, the influence of the intra- and extra-cellular fluid content on the measured bio-impedance depends on the frequency of the injected current. This allows a characterization of the electrical properties of the biological tissue according to the Cole-Cole model. Using measurements at multiple frequencies allows the approximation by interpolation of the electrical properties of the tissue at direct current (DC, frequency of zero Hz) when the extracellular fluid content is the main component of the impedance.

Where, in alternative or additional embodiments, the apparatus 2 is to be used to monitor the subject for dehydration, the overall resistance of the tissue (i.e. including both the intra-cellular $R_i$ and extra-cellular $R_e$ components) or the intra-cellular resistance $R_i$ can be determined from the measured biological tissue impedance.

The estimation of $R_e$ and/or $R_i$ values from impedance measurements can be performed by a processing unit in the control unit 6. The control unit 6 can also implement the method described below and shown in FIG. 2. Alternatively, the control unit 6 can transmit the impedance measurements or estimated $R_e$ and/or $R_i$ values to another apparatus (such as a smart phone, laptop computer, desktop computer or other processing device) that comprises a processing unit that processes the impedance measurements to produce $R_e$ and/or $R_i$ values (if required) and that implements the other steps in the method shown in FIG. 2.

In alternative implementations, an apparatus that comprises two spatially and electrically separated electrodes for surgical implantation into the tissue of a subject's body can be used to collect the bio-impedance measurements. The person skilled in the art will also be aware of other types of systems to that shown in FIG. 1 that can be used to provide bio-impedance measurements.

Figure 2:
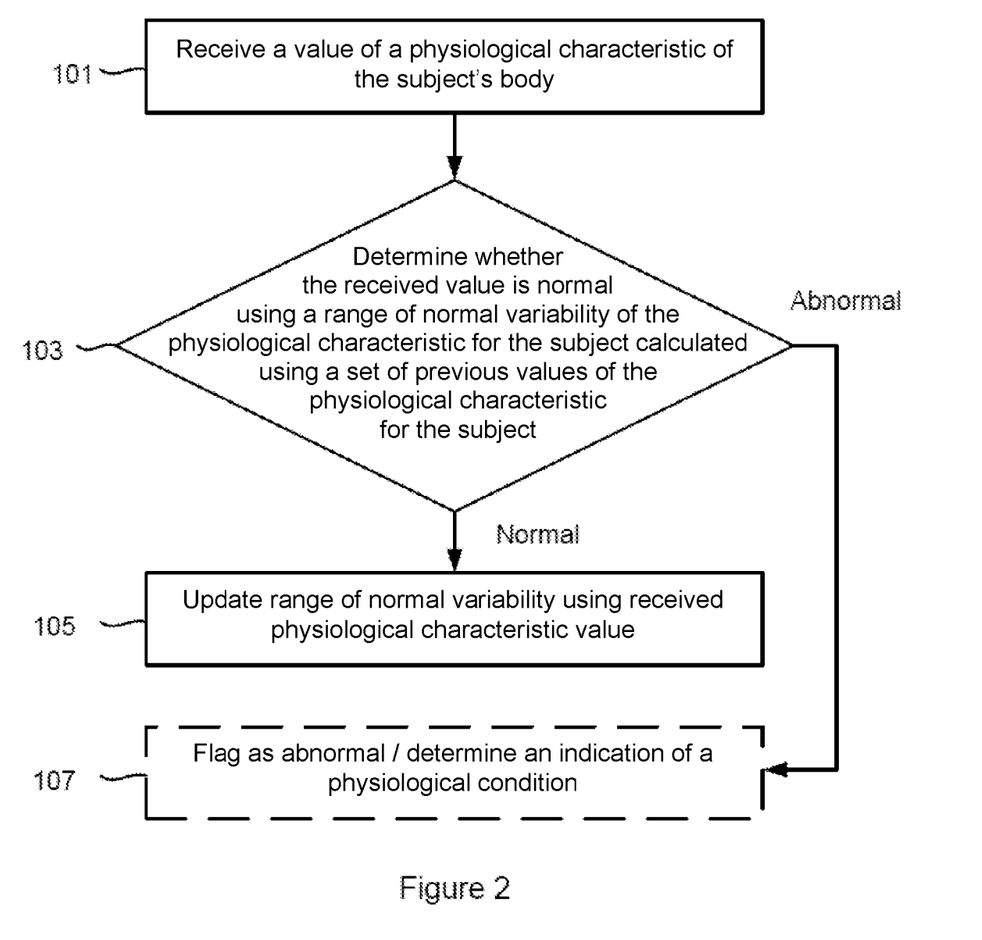
FIG. 2 is a flow chart illustrating a method for use in monitoring a physiological characteristic of a subject according to a general embodiment of the invention.

FIG. 2 shows a method for use in monitoring a physiological characteristic of the body of a subject according to an embodiment of the invention.

In step 101, a new value of the physiological characteristic of the body of the subject is received or obtained, for example from bio-impedance measurement apparatus 2 which measures the impedance of tissue to a small current flowing between two electrodes. In some embodiments, the value of the physiological characteristic is the value of the resistance of fluid in a part of the subject's body. In preferred embodiments, the value of the resistance of fluid is the resistance $R_e$ of extracellular fluid in the part of the body of the subject, and more preferably, $R_e$ is the resistance of extracellular fluid in the lungs of the subject. However, in alternative embodiments, the value of the physiological characteristic can be a weight measurement, heart rate measurement, blood pressure measurement or temperature measurement, etc.

In step 103, the received physiological characteristic value is checked against a range of normal variability of that characteristic for the subject and it is determined whether the received physiological characteristic value is normal. The range of normal variability of that characteristic for the subject is calculated from a set of previously-obtained physiological characteristic values (and particularly, previously-obtained values that were considered to be normal, i.e. not considered to be abnormally high or low). In some embodiments, the range of normal variability can be defined by an upper bound and a lower bound which are derived from the previous normal physiological characteristic values for the subject. The range of normal variability of the characteristic for the subject can also be derived using information on the expected variability of the physiological characteristic values in a sample of representative subjects.

If the physiological characteristic value is found to be normal, in step 105 the received characteristic value is included in the set of previously-obtained normal physiological characteristic values and it is used to update the range of normal variability for the subject. Adapting the range based on newly-collected characteristic values classified as normal for the subject personalizes the range to the subject over time.

The criteria for determining whether a received physiological characteristic value is normal can depend on whether the method is being used to monitor for high values or low values of the physiological characteristic. For example, some physiological conditions, such as excess fluid accumulation in the lungs, result in lower values of the resistance due to extracellular water in the body of the subject. In this case, where the method is monitoring the subject for excess fluid accumulation (and also for recovery from excess fluid accumulation), the method is directed to generally treat low values as being abnormal and indicative of the degree to which fluid is accumulating. However, other physiological conditions, such as dehydration, result in higher values of the resistance of the body of the subject. In this case, the method is to monitor for dehydration and generally treats high values as being abnormal and indicative of the degree to which the subject is dehydrated.

In some embodiments, a number of consecutive high or low values (as appropriate for the condition being monitored for) may need to be received before a determination is made that a high or low received value is abnormal. Thus, even where a received value is outside the range of normal variability, it is not immediately classified as being abnormal, which means that erroneous measurements due to incorrect sensor placement or inconsistent measurement conditions do not trigger false alarms.

In some embodiments, if the physiological characteristic value is found to be abnormal in step 103, then the measurement can be flagged as such (e.g. reported to the subject or physician). In some embodiments, particularly where the method is directed to identify excess extracellular fluid accumulation, an indication of a physiological condition which is correlated to the physiological characteristic (in this case the fluid content or accumulation in the part of the subject's body) can be determined from the physiological characteristic value.

Thus, the method in FIG. 2 makes use of the subject's measurement history to model variability of a particular physiological characteristic (e.g. resistance measurements) for that subject and therefore automatically personalize the monitoring algorithm in order to increase the accuracy of the output. After an initialization period, in which some measurements of the particular physiological characteristic are collected for the subject, a healthy physiological characteristic value and a variance of the measurements of the subject are estimated based on previous measurements of that subject. The subject-specific variability measure is used to set up values for the boundaries for the discrimination between healthy (normal) values and abnormal values. To avoid the influence of abnormal values in the healthy physiological characteristic and variability estimations, values marked as abnormal are excluded from the subject's history used for these estimations. When previous values are incorrectly classified as normal due to an unfortunate initialization (i.e. the subject started the measurement period whilst already suffering from a physiological condition that resulted in abnormal physiological characteristic values), the algorithm can also quickly adapt the variability bounds as measurements are taken when the subject is recovering.

Figure 3:
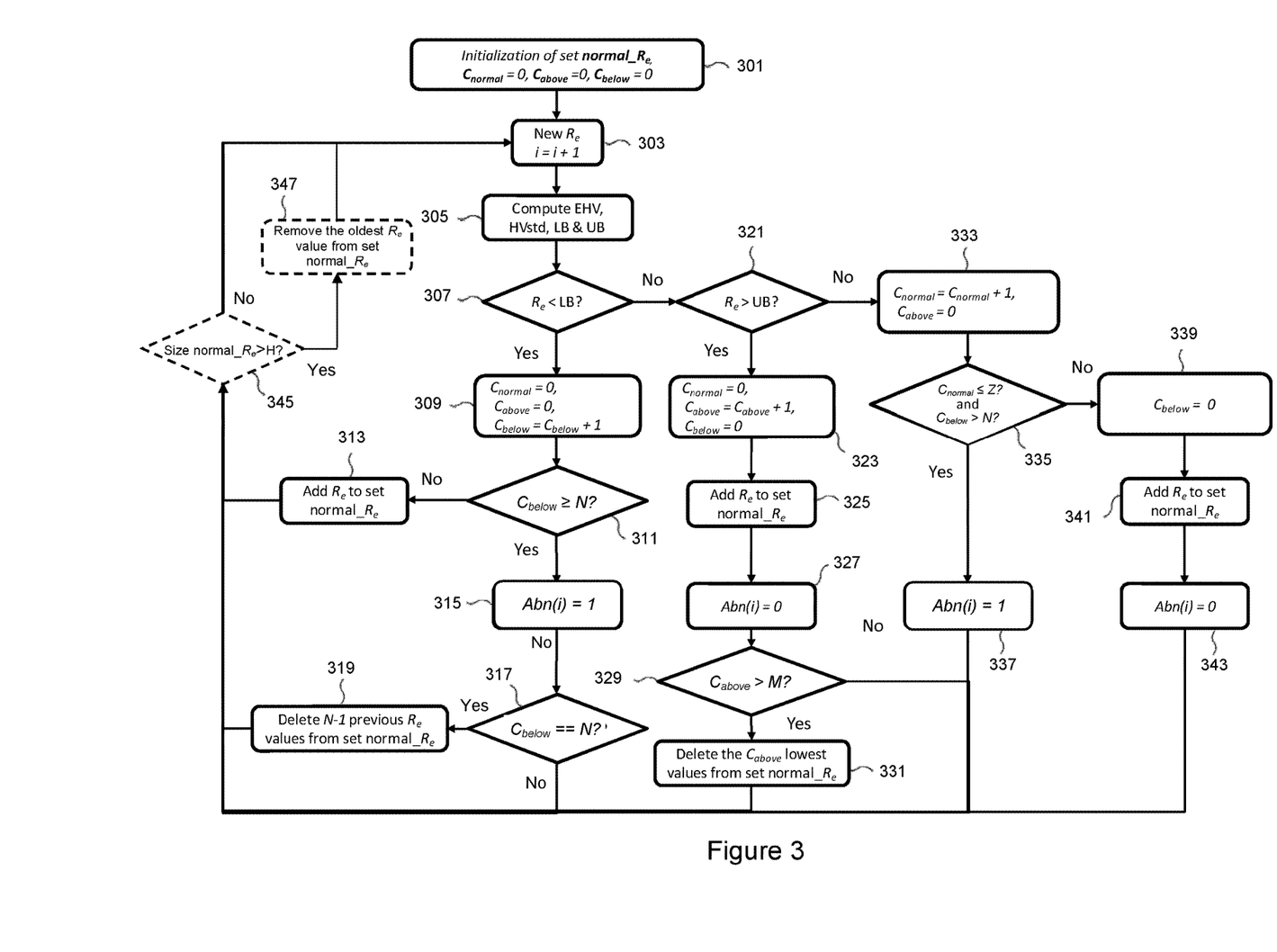
FIG. 3 is a flow chart illustrating the implementation of steps 101-107 of FIG. 2 according to a first specific embodiment of the invention.

FIG. 3 shows an algorithm for implementing steps 101-107 of the method in FIG. 2 according to a first specific embodiment of the invention. In this specific embodiment, the method monitors for extracellular fluid accumulation (i.e. abnormally low resistance values), and thus the physiological characteristic values are extra-cellular fluid resistance ($R_e$) values. An initialization step 301 is performed prior to the first $R_e$ value being received. During this initialization step a set of previously received normal $R_e$ values is formed from a plurality of (e.g. four) previously-collected (and possibly consecutive) $R_e$ values. The values of three counters, denoted $C_{normal}$, $C_{below}$ and $C_{above}$ are set to 0. These counters are used to track how many consecutive $R_e$ values have occurred that are within, below or above the range of normal variability respectively. The method of FIG. 3 therefore begins at step 303 when the next $R_e$ value is received.

At step 303, which corresponds generally to step 101 above, a new $R_e$ value is received. New $R_e$ values could be received each day, although it will be appreciated that $R_e$ values could be received more or less frequently, as appropriate to the subject or health condition being monitored.

At step 305, the algorithm computes several parameters from the $R_e$ values in the set of previously-collected normal $R_e$ values. In particular, an expected healthy value (EHV) of $R_e$ for the specific subject 4, a measure of the Healthy Value variation ($HV_{std}$) and the range of normal variability of $R_e$ defined in terms of an upper bound UB and a lower bound LB for the subject 4 are calculated. As shown in FIG. 3, this step is performed each time a new $R_e$ value is received (although it will be appreciated that it can be performed prior to a new $R_e$ value being received). EHV is calculated from the set of previously received $R_e$ values that were found to be normal and that have been stored in a memory of the control unit 6. Preferably EHV is an average, e.g. the mean, of this set of previously received normal $R_e$ values (hereafter denoted by Normal_$R_e$), as represented by the equation:

$$EHV = mean(Normal\_R_e) \quad \text{Equation 1}$$

although a mode or median could alternatively be used.

$HV_{std}$ is computed by calculating a measure of the variation of the set Normal_$R_e$. Preferably this measure of the variation is the standard deviation of the set Normal_$R_e$, although other measures of variation could be used.

In some embodiments the measure of the Healthy Value variation, $HV_{std}$, is equal to the standard deviation (std) of the set Normal_$R_e$. In some embodiments, however, training data obtained from a training group of further subjects who did not have fluid accumulation in their lungs when the training data was acquired is used to restrict the standard deviation of the set of previously received normal $R_e$ values. This means that $HV_{std}$ is not necessarily equal to the standard deviation of the set Normal_$R_e$.

In this embodiment, a training set of $R_e$ values (hereafter denoted by Training_$R_e$) for the training group was previously obtained, and maximum and minimum coefficients of variance $CV_{max}$ and $CV_{min}$ respectively for the set Training_$R_e$ were calculated by estimating the confidence intervals at a confidence level (e.g. 50%, 95%, 99%, etc.) of the coefficient of variance of the training $R_e$ values. $HV_{std}$ is then computed in step 305 according to the following equation:

$$HV_{std} = std(Normal\_R_e)$$

$$\text{If } HV_{std} < (CV_{min} * EHV) \text{ then } HV_{std} = CV_{min} * EHV$$

$$\text{If } HV_{std} > (CV_{max} * EHV) \text{ then } HV_{std} = CV_{max} * EHV \quad \text{Equation 2}$$

The lower bound LB and upper bound UB of the normal range of variability are then calculated according to $$LB = EHV - HV_{std}$$

$$UB = EHV + HV_{std} \quad \text{Equation 3}$$

In step 307 the algorithm determines whether the received $R_e$ value is below the value of LB calculated in step 305. If $R_e$ is below LB, then the algorithm proceeds to step 309 in which 1 is added to the value of counter $C_{below}$, while the values of the two other counters $C_{normal}$ and $C_{above}$ are set (reset) to 0.

After the counters have been updated in step 309, in step 311 the algorithm checks whether the updated value of $C_{below}$ is greater than or equal to a predefined threshold N. The value N of the threshold determines how many consecutive $R_e$ values that are below the lower bound of the range of normal variability need to be received before the algorithm indicates that an abnormal $R_e$ measurement has been received.

If $C_{below}$ is less than N, then the algorithm moves to step 313 in which the current $R_e$ value is added to the set Normal_$R_e$. This completes the algorithm until the next $R_e$ value is received, when it begins again at step 303. Thus, even though the current $R_e$ value is lower than the lower bound LB of the normal range (and thus potentially indicative of higher fluid content in the part of the subject's body), this $R_e$ value is still classified as 'normal' and is added to the set Normal_$R_e$ to be used in subsequent iterations of step 305 to calculate the updated values of EHV, $HV_{std}$, LB and UB. The use of this threshold N means that one or more (but less than N) erroneous low $R_e$ values that might result from, for example, an incorrect positioning of the electrodes on the body of the subject or the subject being in the wrong posture, do not lead to the algorithm to indicate that there is excess fluid in the part of the body being monitored.

N can take any positive integer value, however the larger the value of N, the longer it will take the algorithm to detect a potentially significant accumulation of fluid. On the other hand, for smaller values of N, the algorithm will be more likely to generate false alarms on the basis of minor and short-lived decreases in $R_e$ that are not clinically significant (for example as a result of incorrect electrode placement or the subject being in the wrong posture). The optimum value of N will depend on how frequently a new value is received. In the case that one value is obtained per day, preferably N is between 3 and 15. In some embodiments N is adapted to be specific to the particular subject If, however, at step 311 $C_{below}$ is found to be greater than or equal to N, indicating that N or more consecutive received $R_e$ values have been below LB, the algorithm moves to step 315 in which the current (i.e. Nth consecutive value below the LB) $R_e$ value is marked as 'abnormal' (i.e. an abnormal indicator, Abn(i) is set to 1). Then, at step 317 the algorithm determines whether the value of $C_{below}$ is equal to N. If it is not equal to N, then the algorithm is complete until the next $R_e$ value is received.

If, on the other hand, at step 317 it is determined that $C_{below}$ is equal to N, then the N−1 previous received $R_e$ values most recently added to the set Normal_$R_e$ are deleted from the set Normal_$R_e$ at step 319. The number of previously received $R_e$ values deleted from the set Normal_$R_e$ in this step may, in some embodiments, be more or fewer than N−1.

The step of deleting the N−1 previous received $R_e$ values from the set Normal_$R_e$ (which would have been added through successive occurrences of step 313) means that $R_e$ values which may be only slightly below the range of expected variability but which are later found to be part of a decreasing trend likely to be indicative of pulmonary oedema are not used when calculating the range of normal variability for subsequent received $R_e$ values. This ensures, as far as possible, that only healthy values are used to calculate the range of normal variability. After performing step 319 the algorithm is complete until the next $R_e$ value is received, when it begins again at step 303.

Returning to step 307, if the received $R_e$ value was not found to be below LB, at step 321 the algorithm determines whether $R_e$ is above UB. If $R_e$ is found to be above UB, 1 is added to the value of $C_{above}$, while $C_{normal}$ and $C_{below}$ are set (reset) to 0, at step 323.

After the counters have been updated, in step 325 the algorithm adds the current $R_e$ value to the set Normal_$R_e$. Since the $R_e$ value has been determined to be normal, it is flagged as such at step 327 (i.e. the abnormal indicator Abn(i) is set to 0).

Then, in step 329, the algorithm checks whether the value of $C_{above}$ is greater than a predefined threshold M. If it is not, then the algorithm is complete until the next $R_e$ value is received, when it begins again at step 303. If, on the other hand, it is determined at step 329 that $C_{above}$ is greater than M, then at step 331 the algorithm deletes the $C_{above}$ smallest $R_e$ values from the set of previously received normal $R_e$ values. This step allows the algorithm to quickly adapt UB and LB in cases where the received $R_e$ values are steadily increasing, for example when the subject is recovering from pulmonary oedema. In some embodiments more or fewer than $C_{above}$ of the smallest values may be deleted from the set Normal_$R_e$ in step 331. After performing step 331 the algorithm is complete until the next $R_e$ value is received, when it begins again at step 303.

It will be appreciated that M may in principle take any positive integer value, however the larger the value of M is, the longer it will take the algorithm to adapt UB and LB to steadily increasing $R_e$ values when a patient is recovering. On the other hand, if M is too small, then this could lead to UB and LB being adjusted unnecessarily due to minor and short-lived increases in $R_e$ that are not clinically significant. Preferably M is between 3 and 15. In some embodiments M is adapted to be specific to the particular subject.

Returning to step 321, if it is determined that the received $R_e$ value is not above the UB (i.e. it is between LB and UB), then in step 333 1 is added to the value of $C_{normal}$, the value of $C_{above}$ is set (reset) to 0, and the value of $C_{below}$ is maintained.

Then, in step 335 the algorithm checks whether (a) the value of $C_{below}$ is greater than the predetermined threshold N, and (b) the value of $C_{normal}$ is less than or equal to a predetermined threshold Z. If it is found that both (a) and (b) are true, then the algorithm proceeds to step 337 in which the received $R_e$ value is marked as abnormal (i.e. the abnormal indicator, Abn(i) is set to 1). This completes the algorithm until the next $R_e$ value is received.

If, on the other hand, in step 335 at least one of the conditions (a) and (b) is not met, then the algorithm proceeds to step 339 in which $C_{below}$ is set to zero. The received $R_e$ value is determined to be normal and in step 341 is added to the set Normal_$R_e$. At step 343 it is therefore not flagged as abnormal (i.e. the abnormal indicator Abn(i) is set to 0). This completes the algorithm until the next $R_e$ value is received, when it begins again at step 303.

The additional check represented by step 335 ensures that up to Z apparently normal $R_e$ values which follow immediately after a series of consecutive $R_e$ values that are below LB does not reset the $C_{below}$ counter. In this circumstance it may be that the up to Z apparently normal $R_e$ values are erroneous (for example if the electrodes were not attached correctly or in the correct position, or if the subject is in the wrong posture), and if the $C_{below}$ counter were to be reset on the basis of such erroneous values this could lead to the accumulation of fluid being missed. The present embodiment guards against such false negatives by disregarding incongruous normal values. Preferably Z is between 1 and 10. It will be appreciated that if Z is too large then the algorithm may be slower to detect that the subject is recovering from fluid accumulation.

In some embodiments it may be desirable to limit the size of the set Normal_$R_e$. Such embodiments may include the optional additional steps 345 and 347, as shown in the dashed boxes in FIG. 3. In step 345 the algorithm determines whether the size of the set Normal_$R_e$ is greater than a pre-defined threshold H. If it is not, then no action is taken and the algorithm is complete until a new $R_e$ value is received in step 303.

If the size of the set Normal_$R_e$ is determined to be greater than H, then the oldest $R_e$ value in Normal_$R_e$ is deleted (step 347). The algorithm then begins again at step 303. This step ensures that the set Normal_$R_e$ only ever contains a maximum of H values, which may be necessary in view of the amount of memory available to store this set. It will be appreciated that H may in principle take any positive integer value, however the larger the value of H is, the more accurate the estimated healthy $R_e$ value and measure of expected variability of $R_e$ for the subject is likely to be. H may be between 25 and 100. In some embodiments H is adapted to be specific to the particular subject.

If the subject is already suffering from fluid accumulation when the initial plurality of $R_e$ values used in step 301 are obtained, the algorithm may not be able to detect when there is excess fluid until a period of recovery has taken place. To avoid this situation, some embodiments employ a "smart initialization" process as described in U.S. provisional patent application No. 61/657,217 filed on 8 Jun. 2012. The normal, healthy thoracic impedance of a specific patient depends on several factors including body dimensions, gender and fat mass and can therefore to some extent be predicted from measurements of these factors. The smart initialization process uses prediction equations based on patient characteristics to determine an expected initial value of $R_e$ for a specific subject. Then, when the algorithm first performs step 305, the initial value of EHV is calculated as a weighted average of the expected initial value of $R_e$ and the initial plurality of $R_e$ values.

Figure 4:
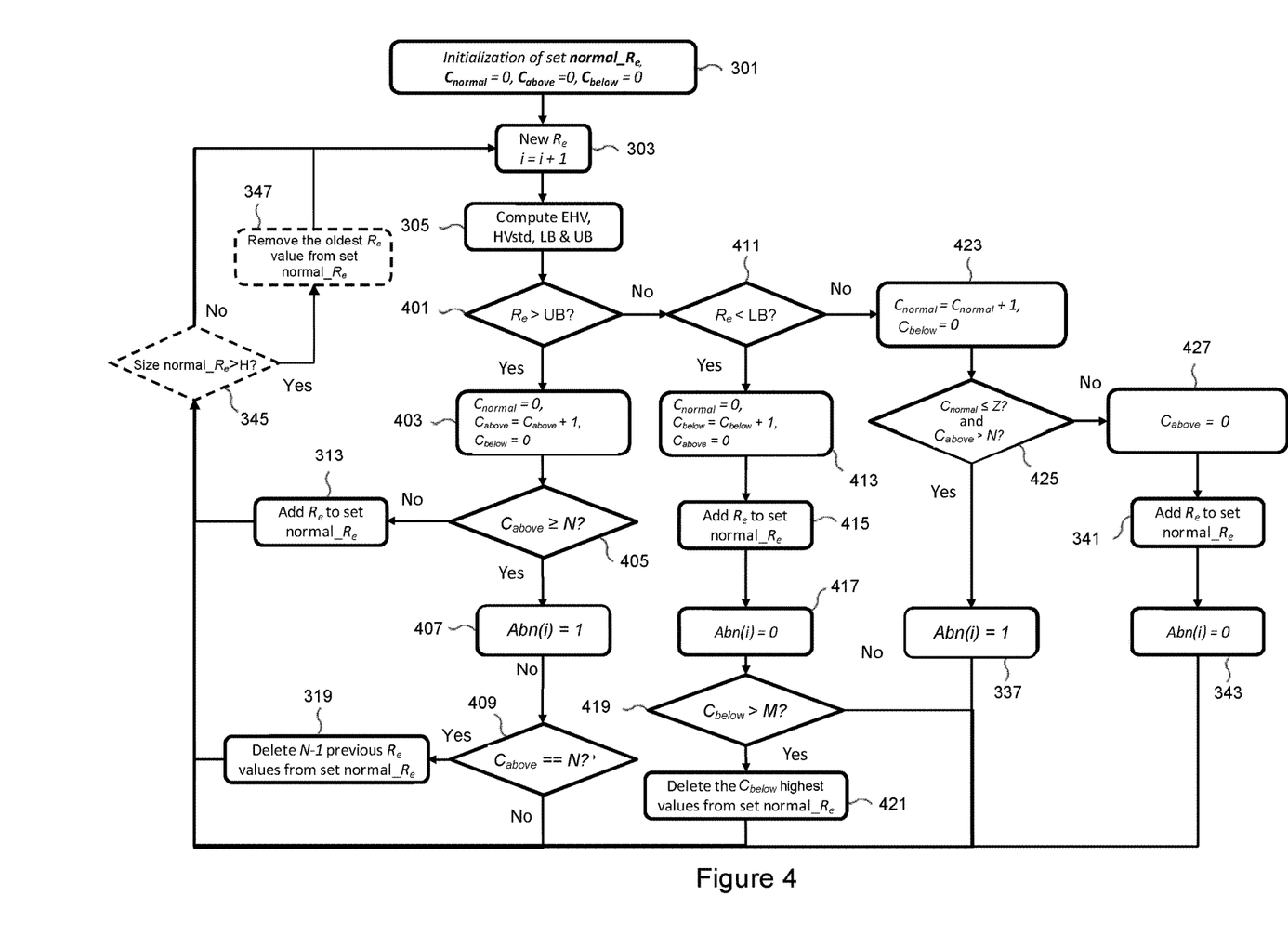
FIG. 4 is a flow chart illustrating the implementation of steps 101-107 of FIG. 2 according to a second specific embodiment of the invention.

As described above, in some situations increases of $R_e$ above EHV may be of interest, since such increases can be indicative of, for example, dehydration. FIG. 4 shows an algorithm for implementing steps 101-107 of the method in FIG. 2 according to a second specific embodiment of the invention. The algorithm of FIG. 4 is the same as that of FIG. 3, except that steps 307, 309, 311, 315 and 317 are replaced by steps 401 to 409 respectively, steps 321 to 331 are replaced by steps 411 to 421 respectively, and steps 333, 335 and 339 are replaced by steps 423 to 427 respectively. These steps will now be described using the assumption that the rest of the algorithm operates as described above in relation to FIG. 3.

After EHV, $HV_{std}$, LB and UB have been computed by the FIG. 4 algorithm in step 305, in step 401 the algorithm determines whether the received $R_e$ value is above UB. If $R_e$ is above UB, then the algorithm proceeds to step 403 in which 1 is added to the value of counter $C_{above}$, while the values of the two other counters $C_{normal}$ and $C_{below}$ are set (reset) to 0.

Then, in step 405, the algorithm checks whether the updated value of $C_{above}$ is greater than or equal to the predefined threshold N. If $C_{above}$ is less than N, then the algorithm moves to step 313 in which the current $R_e$ value is added to the set Normal_$R_e$. This completes the algorithm until the next $R_e$ value is received, when it begins again at step 303.

In this embodiment, N can take the same value as in the first specific embodiment, however it will be appreciated that a different value of N may be appropriate for monitoring dehydration as compared to that which is appropriate for monitoring fluid accumulation.

If at step 405 $C_{below}$ is found to be greater than or equal to N, indicating that N or more consecutive received $R_e$ values have been above UB, the algorithm moves to step 407 in which the current (i.e. Nth consecutive value above the UB) $R_e$ value is marked as 'abnormal' (i.e. an abnormal indicator, Abn(i) is set to 1).

Then, at step 409 the algorithm determines whether the value of $C_{above}$ is equal to N. If it is not equal to N, then the algorithm is complete until the next $R_e$ value is received.

If, on the other hand, at step 409 it is determined that $C_{above}$ is equal to N, then the N-1 previous received $R_e$ values most recently added to the set Normal_$R_e$ are deleted from the set Normal_$R_e$ at step 319. After performing step 319 the algorithm is complete until the next $R_e$ value is received, when it begins again at step 303.

Returning to step 401, if the received $R_e$ value was not found to be above UB, at step 411 the algorithm determines whether $R_e$ is below LB. If $R_e$ is found to be below LB, 1 is added to the value of $C_{below}$, while $C_{normal}$ and $C_{above}$ are set (reset) to 0, at step 413.

After the counters have been updated, in step 415 the algorithm adds the current $R_e$ value to the set Normal_$R_e$. Since the $R_e$ value has been determined to be normal (i.e. it is not indicative of dehydration), it is flagged as such at step 417 (i.e. the abnormal indicator Abn(i) is set to 0).

Then, in step 419, the algorithm checks whether the value of $C_{below}$ is greater than a predefined threshold M. If it is not, then the algorithm is complete until the next $R_e$ value is received, when it begins again at step 303.

If, on the other hand, it is determined at step 419 that $C_{below}$ is greater than M, then at step 421 the algorithm deletes the $C_{below}$ highest $R_e$ values from the set of previously received normal $R_e$ values. This step allows the algorithm to quickly adapt UB and LB in cases where the received $R_e$ values are steadily decreasing, for example when the subject is recovering from dehydration. After performing step 421 the algorithm is complete until the next $R_e$ value is received, when it begins again at step 303.

In this embodiment M can be the same value as in the first specific embodiment, however it will be appreciated that a different value of M may be appropriate for monitoring dehydration as compared to that which is appropriate for monitoring fluid accumulation.

Returning to step 411, if it is determined that the received $R_e$ value is not below the LB (i.e. it is between LB and UB), then in step 423 1 is added to the value of $C_{normal}$, the value of $C_{below}$ is set (reset) to 0, and the value of $C_{above}$ is maintained.

Then, in step 425 the algorithm checks whether (a) the value of $C_{above}$ is greater than the predetermined threshold N, and (b) the value of $C_{normal}$ is less than or equal to a predetermined threshold Z. If it is found that both (a) and (b) are true, then the algorithm proceeds to step 337 in which the received $R_e$ value is marked as abnormal (i.e. the abnormal indicator, Abn(i) is set to 1). This completes the algorithm until the next $R_e$ value is received. In this embodiment, the value of Z can be the same as for the first specific embodiment, but it will be appreciated that a different value of Z may be appropriate for monitoring dehydration as compared to that which is appropriate for monitoring fluid accumulation.

If, on the other hand, in step 425 at least one of the conditions (a) and (b) is not met, then the algorithm proceeds to step 427 in which $C_{above}$ is set to zero. The received $R_e$ value is determined to be normal and in step 341 is added to the set Normal_$R_e$. At step 343 it is therefore flagged as normal (i.e. the abnormal indicator Abn(i) is set to 0). This completes the algorithm until the next $R_e$ value is received, when it begins again at step 303.

Thus, it will be appreciated that in this embodiment $R_e$ values which are above UB are treated in essentially the same manner as $R_e$ values below LB are treated in the first specific embodiment, and vice versa.

It will be appreciated that other modifications to the method of the invention shown in FIG. 3 to enable it to detect abnormal values of $R_e$ are possible. For example, embodiments are also possible in which both $R_e$ values above UB and below LB are treated as potentially of concern (i.e. steps 401 to 409 are performed in place of steps 321 to 421 in the FIG. 3 algorithm. Such embodiments would monitor for both fluid accumulation and dehydration simultaneously.

Figure 5:
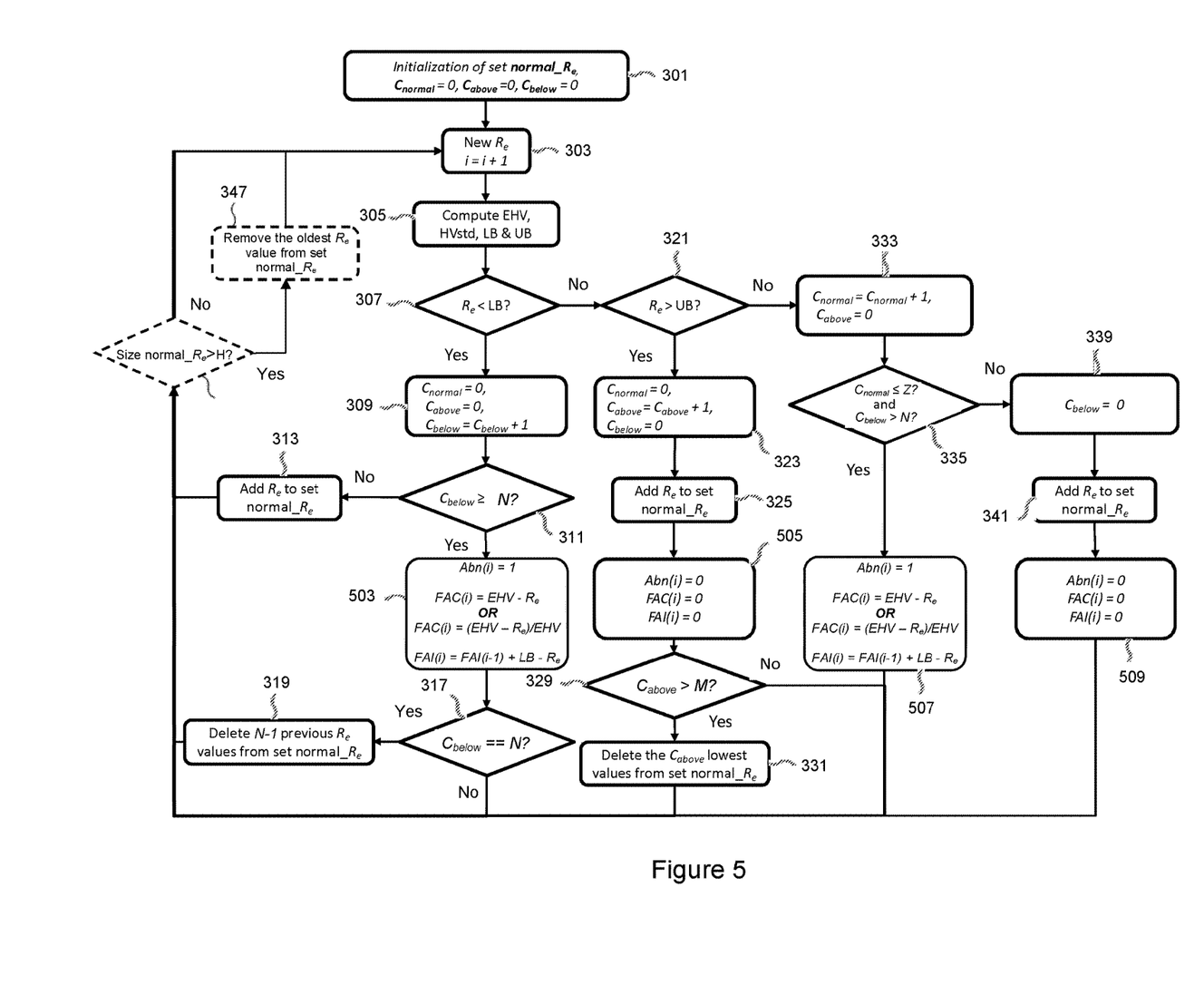
FIG. 5 is a flow chart illustrating the implementation of steps 101-107 of FIG. 2 according to a third specific embodiment of the invention.

FIG. 5 shows an algorithm for implementing steps 101-107 of the method in FIG. 2 according to a third specific embodiment of the invention. The algorithm of FIG. 5 is the same as that of FIG. 3, except that steps 315, 327, 337 and 343 are replaced by steps 503, 505, 507 and 509 respectively. These steps will now be described using the assumption that the rest of the algorithm operates as described above in relation to FIG. 3.

If the FIG. 5 algorithm has determined at step 307 that the received $R_e$ value is less than LB, and at step 311 that the updated value of $C_{below}$ is greater than or equal to N, then it performs step 403 in which an indication of the fluid content of the part of the body of the subject being monitored is determined, in addition to the received $R_e$ value being marked as abnormal. This indication can be a fluid accumulation content (FAC) and/or a fluid accumulation index (FAI). FAC and FAI can be calculated using the following equations:

$$FAC(i) = EHV - R_e(i) \qquad \text{Equation 4}$$

$$FAI(i) = FAI(i-1) + (LB - R_e(i)) \qquad \text{Equation 5}$$

where i is an index corresponding to the current received $R_e$ value (and hence $R_e(i-1)$ corresponds to the previous received $R_e$ value).

The FAC is indicative of the amount of fluid accumulation at the time of that $R_e$ measurement (e.g. for a given day (in embodiments where one $R_e$ value is generated per day by the bio-impedance measurement apparatus)), while the FAI is indicative of the persistence of the fluid accumulation.

If the FIG. 5 algorithm has determined at step 321 that the received $R_e$ value is above UB, then following the addition of the received $R_e$ value to the set Normal_$R_e$ at step 325 the algorithm performs step 405. In step 405 the FAC and the FAI are set to zero, and the $R_e$ measurement is marked as normal.

If the received $R_e$ value is determined to be between LB and UB and at step 311 it is found to be true that both (a) $C_{normal}$ is equal to 1 and (b) $C_{below}$ is greater than N, then the algorithm performs step 407 in which the fluid accumulation content (FAC) and the fluid accumulation index (FAI) are calculated using equations 4 and 5, as well as marking the received $R_e$ value as abnormal. If at step 335 it is determined that at least one of (a) and (b) is not true, then after adding the received $R_e$ value to the set Normal_$R_e$ at step 341 the algorithm sets the FAC and the FAI to zero in step 409 and marks the $R_e$ measurement as normal.

Thus, when a given $R_e$ value is found to be abnormal, the FIG. 5 algorithm calculates the FAC and FAI using this value. When, on the other hand, an $R_e$ value is added to the set Normal_$R_e$, the FIG. 4 algorithm sets the values of the FAC and FAI to zero. The use of FAC and FAI improves the sensitivity of the algorithm in detecting pulmonary congestion.

In some embodiments (which are also illustrated in FIG. 5) the FAC is calculated relative to EHV, the expected healthy value of $R_e$ for the subject. Thus in these embodiments equation 4 is replaced by:

$$FAC(i) = (EHV - R_e)/EHV \qquad \text{Equation 6}$$

This makes the algorithm more robust against large differences in the magnitude of EHV between subjects.

Although the specific embodiments of the invention in FIGS. 3 and 5 have been described above as being preferably for use in monitoring the accumulation of extra-cellular water in the lungs of a subject 4, it will be appreciated that the invention can be used in monitoring the accumulation of fluid (whether extra-cellular, intra-cellular or combined) of other parts of the body of the subject 4. For example, a bio-impedance measurement apparatus 2 can be provided for use on the wrist, ankle or other joint of a subject 4 (for example as part of an assessment of inflammation of the joint) so as to generate $R_e$ values for these body parts.

There is therefore provided a method and apparatus that allow a subject to be monitored so as to detect and/or predict the onset of or recovery from clinically significant conditions using measurements of one or more physiological characteristics of the subject.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for use in monitoring for low values of a physiological characteristic of a subject, the method comprising:
receiving, at a configured processing unit, a value of the physiological characteristic of the subject from a bio-impedance sensor configured to be applied to the skin of the subject's body, wherein the sensor includes two pairs of electrodes including a first pair and a second pair, wherein the first pair and the second pair are adapted for placement on the skin of the subject's body to thereby measure a differential potential across the skin of the subjects body;
calculating, by the configured processing unit, a range of normal variability of the physiological characteristic for the subject having a lower bound and an upper bound using a set of previous values of the physiological characteristic for the subject obtained from the bio-impedance sensor or a different bio-impedance sensor;
determining, by the configured processing unit, whether the received physiological characteristic value is below the lower bound or above the upper bound and:
in response to determining that the received physiological characteristic value is below the lower bound:
incrementing a below normal counter;
determining whether the below normal counter meets or exceeds a first threshold N, and: in response to determining that the below normal counter does not meet or exceed the first threshold N, adding the received physiological characteristic value to the set of previous values of the physiological characteristic for the subject;
in response to determining that the below normal counter exceeds the first threshold number N, refraining from adding the received physiological characteristic value to the set of previous values; and
in response to determining that the below normal counter meets but does not exceed the first threshold number N, deleting a number of the previous values of the set that were most recently added to the set and refraining from adding the received physiological characteristic value to the set of previous values; and in response to determining that the received physiological characteristic value is above the upper bound:
setting the below normal counter to zero; and
adding the received physiological characteristic value to the set of previous values; and
recalculating, by the configured processing unit, the range of normal variability of the physiological characteristic using the set of previous values of the physiological characteristic of the subject.

2. A method as claimed in claim 1, wherein recalculating the range of normal variability comprises calculating a standard deviation of the set of previous physiological characteristic values.

3. A method as claimed in claim 1, further comprising:
in response to determining that the received physiological characteristic value is below the lower bound:
setting an above normal counter to zero; and
in response to determining that the received physiological characteristic value is above the upper bound:
incrementing the above normal counter;
determining whether the above normal counter satisfies a second threshold number M; and
in response to determining that the above normal counter satisfies a second threshold number M, deleting a number equal to the above normal counter of lowest values of the previous values of the set.

4. A method as claimed in claim 3, further comprising:
determining, by the configured processing unit, whether the received physiological characteristic value is between the lower bound and the upper bound; and
in response to determining that the received physiological characteristic value is between the lower bound and the upper bound:
setting the above normal counter to zero;
incrementing a normal counter;
determining, by the configured processing unit, if (i) the normal counter is less than or equal to a third threshold value, Z, and (ii) the below normal counter is greater than the first threshold value, N; and
in response to determining that at least one of (i) and (ii) is false:
setting the below normal counter to zero and adding the received physiological characteristic value to the set of previous values; and
in response to determining that both (i) and (ii) are true:
discarding the received physiological characteristic value by failing to add it to the set of previous values.

5. A non-transitory computer readable program product, comprising computer readable code embodied therein, the computer readable code being configured such that, on execution by a suitable computer or processor, the computer or processor performs the method described in claim 1.

6. An apparatus for use in monitoring for low values of a physiological characteristic of a subject, the apparatus comprising:
a bio-impedance sensor including two pairs of electrodes including a first pair and a second pair, wherein the first pair and the second pair are adapted for placement on the skin of the subject's body to thereby measure a differential potential across the skin of the subjects body; and
a processing unit configured to:
receive a value, of the physiological characteristic of the subject from the sensor configured to be applied to the subject's body;
calculate a range of normal variability of the physiological characteristic for the subject having a lower bound and an upper bound using a set of previous values of the physiological characteristic for the subject obtained from the bio-impedance sensor or a different bio-impedance sensor;
determine whether the received physiological characteristic value is below the lower bound or above the upper bound and:
in response to determining that the received physiological characteristic value is below the lower bound:
increment a below normal counter;
determine whether the below normal counter meets or exceeds a first threshold N, and;
in response to determining that the below normal counter does not meet or exceed the first threshold N, add the received physiological characteristic value to the set of previous values of the physiological characteristic for the subject;
in response to determining that the below normal counter exceeds the first threshold number N, refrain from adding the received physiological characteristic value to the set of previous values; and
in response to determining that the below normal counter meets but does not exceed the first threshold number N, delete a number of the previous values of the set that were most recently added to the set and refraining from adding the received physiological characteristic value to the set of previous values;
in response to determining that the received physiological characteristic value is above the upper bound:
set the below normal counter to zero; and
add the received physiological characteristic value to the set of previous values; and
recalculate the range of normal variability of the physiological characteristic using the set of previous values of the physiological characteristic for the subject.

7. An apparatus as claimed in claim 6, wherein the processing unit is further configured to calculate a standard deviation of the set of previous physiological characteristic values.

8. An apparatus as claimed in claim 6, wherein the processing unit is further configured to:
in response to determining that the received physiological characteristic value is below the lower bound:
set an above normal counter to zero; and
in response to determining that the received physiological characteristic value is above the upper bound:
increment the above normal counter;
determine whether the above normal counter satisfies a second threshold number M; and
in response to determining that the above normal counter satisfies a second threshold number M, delete a number equal to the above normal counter of lowest values of the previous values of the set.

9. The apparatus as claimed in claim 8, wherein the processing unit is further configured to:
determine whether the received physiological characteristic value is between the lower bound and the upper bound; and in response to determining that the received physiological characteristic value is between the lower bound and the upper bound:
set the above normal counter to zero;
increment a normal counter;
determine, using the configured processing unit, if (i) the normal counter is less than or equal to a third threshold value, Z, and (ii) the below normal counter is greater than the first threshold value, N; and
in response to determining that at least one of (i) and (ii) is false:
set the below normal counter to zero and adding the received physiological characteristic value to the set of previous values; and
in response to determining that both (i) and (ii) are true:
discard the received physiological characteristic value by failing to add it to the set of previous values.

* * * * *